United States Patent [19]

Bowers-Daines et al.

[11] Patent Number: 5,209,930
[45] Date of Patent: May 11, 1993

[54] PREPARATION AND USE OF N-IODOPROPARGYL OXYCARBONYL AMINO ACID ESTERS AND DERIVATIVES AS ANTIMICROBIAL AGENTS

[75] Inventors: Margaret M. Bowers-Daines; Barry C. Lange, both of Lansdale, Pa.

[73] Assignee: Rohm and Haas Company, Philadelphia, Pa.

[21] Appl. No.: 625,264

[22] Filed: Dec. 10, 1990

[51] Int. Cl.$^5$ ................................. A61K 7/00
[52] U.S. Cl. .......................... 424/401; 424/78.09; 424/404; 422/37; 426/326; 427/384; 560/16; 560/24; 560/27; 560/29; 560/137; 560/148; 560/160; 560/167
[58] Field of Search ............... 424/404, 401, 667, 668, 424/672, 70, 78.07, 78.09; 514/5, 549, 809, 521, 533, 478; 558/417; 427/384; 560/16, 27, 29, 24, 137, 148, 160, 167

[56] References Cited

U.S. PATENT DOCUMENTS

| | | | |
|---|---|---|---|
| 2,281,612 | 5/1942 | Witte | 514/5 |
| 2,385,394 | 4/1943 | Witte | 424/667 |
| 4,054,668 | 10/1977 | Kirino et al. | 514/549 |
| 4,322,340 | 3/1982 | Shuman et al. | 514/809 |
| 4,592,773 | 6/1986 | Tanaka et al. | 514/521 |
| 4,844,891 | 7/1989 | Rosen et al. | 424/70 |
| 4,945,109 | 7/1990 | Rayudu | 514/478 |
| 5,073,570 | 12/1991 | Tseng | 514/533 |

FOREIGN PATENT DOCUMENTS 56-77209  6/1981  Japan ................... 424/674

Primary Examiner—Thurman K. Page
Assistant Examiner—D. Colucci
Attorney, Agent, or Firm—Michael B. Fein

[57] ABSTRACT

Antimicrobial compounds of the formula $$I-{\equiv}-O-\underset{\underset{R^3}{|}}{\underset{\|}{N}}-\underset{\|}{\overset{R^1}{C}}-\underset{\|}{C}-O-R^2$$

wherein $R^1$ is selected from the group consisting of H, lower ($C_1$–$C_4$)alkyl, alkyl aryl, $CH_2OR$, $CH_2SR$, and $CH(CH_3)OR$; and
R, $R^2$, and $R^3$ are independently selected from H, ($C_1$–$C_4$)alkyl, aryl, arylalkyl, alkaryl, and halopropargyl.

9 Claims, No Drawings

PREPARATION AND USE OF N-IODOPROPARGYL OXYCARBONYL AMINO ACID ESTERS AND DERIVATIVES AS ANTIMICROBIAL AGENTS

BACKGROUND OF THE INVENTION

1. Field of the Invention

This invention relates to the field of antimicrobial agents.

2. Description of the Prior Art

Slager, U.S. Pat. No. 3,923,870, discloses iodopropargyl oxycarbamates which are N-substituted with alkyl, aryl, or alkylaryl groups as having fungicidal activity.

Ger. Offen. DE 2515091 (1975), Ciba Geigy AG, discloses microbicidal anilides which are acylanilides which have an amino acid moiety and an iodopropargyl fragment as shown, but the point of attachment of the iodopropargyl fragment is not directly on the amino acid portion of the molecule. These compounds are N-iodopropargyloxy acid amides.

Kokai Tokkyo Koho JP 54/125614 (1979), Shigaken Pharmaceutical Co., Ltd. discloses antimicrobial iodopropargyloxy acid amide derivatives useful for bactericides and agricultural fungicides.

U.S. Pat. No. 4,535,088-A (1985) assigned to Shionogi and Co., shows 2-(3-Iodo)propynyl-amino-thiazole derivatives as useful as antimicrobials, i.e. antibacterial and antifungal agents.

Peptides: Synthesis, Structure and Function: Proc. Am. Pept. Symposium, 7th, (1981), pp 101–4 describes the synthesis of C-iodopropargyl glycine. There is no mention of antibacterial or antifungal activity.

SUMMARY OF THE INVENTION

Many of the antimicrobials of the prior art have toxicity and/or environmental problems.

It is an object of the present invention to provide novel antimicrobial compounds which have improved toxicity profiles and are not harmful to the environment.

These objects, and others which will become apparent from the following disclosure, are achieved by the present invention which comprises in one aspect compounds of the formula

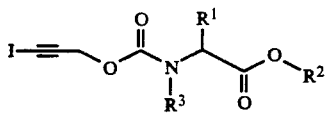

wherein $R^1$ is selected from the group consisting of H, lower ($C_1$-$C_4$)alkyl, alkyl aryl, $CH_2OR$, $CH_2SR$, and $CH(CH_3)OR$; and R, $R^2$, and $R^3$ are independently selected from H, ($C_1$-$C_4$)alkyl, aryl, arylalkyl, and alkaryl.

DETAILED DESCRIPTION OF THE INVENTION AND THE PREFERRED EMBODIMENTS

The compounds of the invention have been discovered to be unexpectedly effective antimicrobials. The compounds are designed to biodegrade down to non-toxic amino acid components.

Some representative compounds include the following:

| TABLE OF COMPOUNDS ($R^3$ = H) | | |
|---|---|---|
| Compound Number | $R^1$ | $R^2$ |
| 1 | H | H |
| 2 | H | $CH_3$ |
| 3 | H | $C_8H_{17}$ |
| 4 | H | $CH_2$—C≡C—I |
| 5 | $CH_3$ | H |
| 6 | $CH_3$ | $CH_3$ |
| 7 | $CH_3$ | $C_8H_{17}$ |
| 8 | $CH_2Ph$ | H |
| 9 | $CH_2Ph$ | $CH_3$ |
| 10 | $CH_2Ph$ | $C_8H_{17}$ |

The compounds of this invention can be prepared by converting the appropriate D- or L-α-amino acid ester hydrochloride to the corresponding 2-isocyanato alkyl ester. The resultant isocyanate compound is reacted with iodopropargyl alcohol to give the N-iodopropargyloxycarbonyl amino acid ester. The free N-iodopropargyloxycarbonyl amino acids are prepared via alkaline hydrolysis of the corresponding ester. Other N-iodopropargyloxycarbonyl amino acid esters are prepared by esterification of the free N-iodopropargyloxycarbonyl amino acid with an appropriate alcohol or alkylhalide utilizing standard known methods.

Iodopropargyl alcohol can be prepared by the procedure described in Bulletin of the Chemical Society of Japan, Ando, T., Shioi, S., Nakagawa, M., (1972) 45, 2611.

The 2-isocyanato alkyl esters are obtained from the corresponding amino acid ester hydrochloride salts by adapting the procedure for preparing 3-isocyanatopropanoyl chloride as described in Organic Synthesis: Collective Volume VI,(1988),715.

As stated above, compositions comprising a compound according to formula I and either an agronomically acceptable carrier, a cosmetic agent, a cutting oil, a soap or synthetic detergent, a stabilizer, a film forming material, or the like have a wide range of utility for protecting against or controlling microorganisms from a wide variety of classes including fungi, bacteria, algae, viruses and yeasts. The preferred utilities of the compositions are to protect wood, paint, adhesive, glue, paper, textile, leather, plastics, cardboard, lubricants, cosmetics, food, caulking, feed and industrial cooling water from microorganisms.

The following lists specific industries and applications of the compounds or compositions:

| Industry | Application |
|---|---|
| Adhesives, sealants | adhesives |
| | caulks |
| | sealants |
| Agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |

| Industry | Application |
|---|---|
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer lactices |
| Formulated consumer & industrial products | air fresheners |
| | fabric softeners |
| | hand cleaners |
| | polishes, floor, furniture, shoe |
| | sponges & towelettes |
| | spray strach |
| | waxes |
| Industrial processing, misc | dry cleaning fluids preservation |
| | electrodeposition paint, baths, rinses. |
| | electrodeposition pre-treatment, post rinses |
| | industrial fluids preservation |
| | pasteurization baths |
| | process aid preservation |
| Industrial water treatment | air washers |
| | cooling towers |
| | cooling water |
| | water cooling |
| Laundry | household laundry products |
| | laundered goods |
| | laundry rinse water |
| | pre-washers |
| | sanitizers-laundry |
| | removers, spot & stain |
| Leather, leather products | leather and hide |
| | leather and hide products |
| Lubricants, hydraulic aids | automotive lubricants and fluids |
| | conveyor lubricants |
| | greases |
| | hydraulic fluids |
| | hydraulic oils |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings | coating emulsions |
| | paints |
| Paper and wood pulp, their products | absorbant materials of paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels | aviation fuels (jet fuel, aviation gas) |
| | burner, diesel and turbine fuel oils |
| | coal slurries |
| | diesel fuel additives |
| | diesel fuels |
| | fuels |
| | gasoline |
| | heating oils |
| | hydrocarbons |
| | kerosene |
| | liquefied petroleum gas |
| | petrochemical feedstocks |
| | petroleum products storage, transportation and production |
| | recycled petroleum products |
| | residual fuel oils |
| | turbine oils |
| Pharmaceutical | topical antifungal and antibacterial |
| Photographic chemicals and process | photographic processing - wash water, rinses |
| | photoplate processing chemicals (developers, stabilizers etc) |
| Printing | fountain solutions (printing) |
| | ink components (pigments, rinses, solvents, etc) |
| | inks |
| Sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents, hand automatic laundry, other |
| | household cleaners |
| | industrial cleaners |
| | liquid soaps, hand, dish, laundry |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | canvas backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |

| Industry | Application |
|---|---|
| Therapeutic (active or preservative) | animal health/veterinary<br>aquaculture<br>dental<br>human health<br>pharmaceutical/therapeutic |
| Water purification | charcoal beds<br>deionization resins<br>filters<br>membranes<br>reverse osmosis membranes<br>ultrafilters<br>water purification<br>water purification pipes, tubing |
| Wood applications | lazures (wood stains)<br>wood<br>wood products |
| Miscellaneous | alcohols<br>bedding incorporating water or gels<br>ceramic<br>contact lens cases-leaching<br>electronic circuitry<br>electronics chemicals<br>enzymes-food production<br>enzymes-industrial<br>gel cushions<br>laboratory reagents<br>marine antifoulants<br>mildewcides<br>mining applications<br>natural rubber latex<br>oil field applications<br>pipes<br>plastics<br>polymer systems<br>polymers and resins (synthetic and natural)<br>reagent preservation<br>rubber<br>rubber products<br>skin remover<br>solid protective/decorative films<br>swimming pools<br>waste treatment<br>water beds |

The amounts of the compound to be used depend on the application. The useful amounts for a particular application are similar to amounts used for other microbicide compounds.

The compound can be used in combination with other microbicides. The term "microbicide" is considered equivalent to "antimicrobial" as used herein.

Suitable methods of application of compounds of formula I to control fungi, bacteria, algae, viruses, yeasts, and the like are in amounts and with carriers, etc., as well known in the art.

The following examples are presented to illustrate a few embodiments of the invention, but are not to be considered as limiting.

EXAMPLE 1

Preparation of N-Iodopropargyloxycarbonyl glycine methyl ester

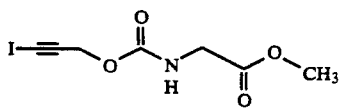

Trichloromethylchloroformate (18.00 ml., 149.2 mmole) was added to a slurry of glycine methyl ester hydrochloride (12.56 g., 100.0 mmole) in anhydrous 1,4-dioxane (200 ml) and refluxed for 5 hours and then stirred at room temperature for 16 hours. The excess trichloromethylchloroformate and 1,4-dioxane were removed from the reaction mixture by distillation under slightly reduced pressure. The resultant residue was distilled to afford the desired intermediate 2-isocyanatoacetic acid methyl ester (10.02 g., 87.1% yield) as a clear colorless liquid. B.P. 67°–68° C. (15–20 mm Hg.); $^1$H-NMR (200 MHz, CDCl$_3$) $\delta_{ppm}$=3.84, s, 3H (—OCH$_3$), 3.97, s, 2H (—N—CH$_2$—C).

The 2-isocyanatoacetic acid methyl ester (10.02 g. 87.06 mmole) was dissolved in anhydrous toluene (100 ml) and treated with an anhydrous toluene (50 ml) solution of iodopropargyl alcohol (15.84 g., 87.05 mmole), followed by 6 drops of di-n-butyl tin dilaurate. The reaction mixture was heated at 85° C. for 17.5 hours. After cooling to room temperature, the heterogeneous reaction mixture was diluted with ethyl acetate. The solution was washed with 3×60 ml. of water, 3×60 ml. of 10% aqueous potassium hydrogen sulfate, 3×60 ml. of saturated aqueous sodium bicarbonate, 60 ml. of saturated aqueous sodium chloride, dried over magnesium sulfate, filtered and concentrated under reduced pressure to afford 25.50 g. (94.7% crude yield) as a yellow crystalline solid. Recrystallization from methylene chloride/hexane gave 12.97 g. of N-iodopropargyloxycarbonyl glycine methyl ester (Compound 2) as a white crystalline solid (m.p. 93.5°–95.0° C.). $^1$H-NMR (200 MHz, CDCl$_3$) $\delta_{ppm}$=3.78, s, 3H (—OCH3), 4.01, d, 2H (—CH$_2$—NH—), 4.86, s, 2H (—CH$_2$—), 5.33, broad s, 1H, (NH). The mother liquor of compound 2 was concentrated under reduced pressure and the residue chromatographed on 200 g. of silica gel and eluted with a 6:1 mixture of 25% methylene chloride in hexane and ethyl acetate to afford 8.43 g. of N-iodopropargyloxycarbonyl glycine methyl ester (compound 2) as a white crystalline solid. This second crop of material had a m.p. 88°–92° C. The combined total yield for this reaction was 82.8%.

EXAMPLE 2

Preparation of N-Iodopropargyloxycarbonyl Glycine

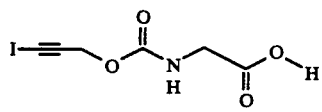

N-Iodopropargyloxycarbonyl glycine methyl ester (Compound 2, 8.03 g., 27.03 mmole) was dissolved in 100 ml. of tetrahydrofuran, cooled to 0° C. with an ice bath and treated during 15 minutes with 30.5 ml. of 1M aqueous lithium hydroxide. The reaction mixture was stirred at 0° C. for 3/4 hr. or until the starting material was no longer present. The reaction progress was monitored by thin layer chromatography (silica gel, methylene chloride/acetic acid 90:10). After the reaction was complete, the aqueous solution was acidified (pH=2) with 10% aqueous potassium hydrogen sulfate (100 ml) and 3N aqueous hydrogen chloride (10 ml.). This mixture was extracted several times with diethyl ether. The ether layers were combined and washed with water, dried over magnesium sulfate, filtered and concentrated under reduced pressure to afford N-iodopropargyloxycarbonyl glycine (Compound 1) as a pale amber oil, which crystallized upon standing (6.63 g., 86.7% yield after drying in vacuo over P$_2$O$_5$). m.p. 108°–110° C.

1H-NMR (200 MHz., DMSOd6) $\delta_{ppm}$=3.67., d, 2H (—NH—C$\underline{H}_2$—), 4.76, s, 2H (C—C$\underline{H}_2$—O), 7.66, t, 1H (N$\underline{H}$).

EXAMPLE 3

Preparation of N-Iodopropargyloxycarbonyl Glycine n-Octyl Ester

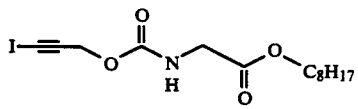

N-Iodopropargyloxycarbonyl glycine (compound 1, 6.50 g., 22.97 mmole) was dissolved in anhydrous acetonitrile (100 ml.), treated with 1,8-diazabicyclo[5.4.0]undec-7-ene (3.5 ml., 23.40 mmole) and stirred at room temperature for 5 minutes. n-Octylbromide (4.00 ml., 23.16 mmole) was added and the reaction mixture was stirred at room temperature for 17 hours, then heated at reflux temperature for 6 hours. The reaction mixture was concentrated under reduced pressure and the resultant residue was dissolved in ethyl acetate. The ethyl acetate solution was washed with water, 5% aqueous citric acid, saturated aqueous sodium bicarbonate, saturated aqueous sodium chloride, dried over magnesium chloride, filtered and concentrated under reduced pressure. The resultant residue was purified utilizing column chromatography (silica gel, 200 g.) and eluted with ethyl acetate/hexane (1:10) to afford N-Iodopropargyloxycarbonyl glycine n-octyl ester (Compound 3) as a clear colorless liquid which crystallized on standing. m.p. 43°-46° C. Elemental Analysis: C$_{14}$H$_{22}$NO$_4$I: Calc'd. C: 42.55, H: 5.61, N: 3.54. Found: C: 43.73, H: 5.62, N: 3.54. (Ethyl acetate was present in 0.5 mole %). 1H-NMR (200 MHz, CDCl$_3$) $\delta_{ppm}$=0.89, m, 3H (—CH$_3$), 1.30, m, 10H (—(CH$_2$)$_5$—CH$_3$), 1.64, m, 2H (—C$\underline{H}_2$—), 4.0,d, J=3.4 Hz., 2H (—N—C$\underline{H}_2$—), 4.1-4.2, m, 2H (—C$\underline{H}_2$—), 4.86, s, 2H (C—C$\underline{H}_2$—O), 5.32, m, 1H (—N$\underline{H}$—). IR (neat) 3460, 2920, 2850, 2200, 1740, 1560, 1480, 1400, 1360, 1200, 1060, 980 cm$^{-1}$.

EXAMPLE 4

Preparation of N-Iodopropargyloxycarbonyl Glycine Iodopropargyl Ester

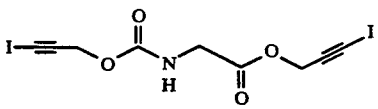

N-Iodopropargyloxycarbonyl glycine (compound 1, 4.96 g., 17.52 mmole) was dissolved in a mixture of methylene chloride and 1,4-dioxane (450 ml., 20 ml. respectively) and cooled to 0° C. with an ice bath. Iodopropargyl alcohol (3.51 g., 19.29 mmole) was added, followed by 4-dimethylaminopyridine (0.22 g., 1.80 mmole) and N-(dimethylaminopropyl)-N'-ethylcarbodiimide hydrochloride (4.17 g., 21.75 mmole). The reaction mixture was stirred at 4° C. for 17 hours. Upon warming to room temperature, the reaction mixture was diluted with methylene chloride, washed with water, 10% aqueous potassium hydrogen sulfate, saturated aqueous sodium bicarbonate, saturated aqueous sodium chloride, dried over magnesium sulfate, filtered and concentrated under reduced pressure to afford N-iodopropargyloxycarbonyl glycine iodopropargyl ester (compound 4) as a white crystalline solid (8.26 g.). m.p. 86°-88° C.; 1H-NMR (200 MHz, CDCl$_3$) $\delta_{ppm}$=4.05, d, J=5.6 Hz., 2H (NH—C$\underline{H}_2$—), 4.89, d, J=10.2 Hz., 4H (C—C$\underline{H}_2$—O), 5.32, m, 1H (—N$\underline{H}$—).

EXAMPLE 5

Preparation of N-Iodopropargyloxycarbonyl Alanine Methyl Ester

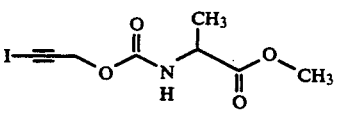

L-Alanine methyl ester hydrochloride (6.00 g., 42.99 mmole) was slurried in anhydrous 1,4-dioxane (125 ml.), treated with trichloromethylchloroformate (7.8 ml., 64.66 mmole) and heated at 55° C. for 20.5 hours. The excess trichloromethylchloroformate and 1,4-dioxane were removed from the reaction mixture by distillation under slightly reduced pressure. The resultant residue was subjected to distillation to afford the desired intermediate 2-isocyanatopropionic acid methyl ester (4.64 g., 83.6% yield) as a clear colorless liquid. B.P. 58° C. (15-20 mm Hg.). 1H-NMR (200 MHz, CDCl$_3$) $\delta_{ppm}$=1.54, d, J=8 Hz., 3H (—CH$_3$), 3.87, s, 3H (—OCH$_3$), 4.13, q, J=8 Hz., 1H(—CH—CH$_3$), IR(neat) 3000, 2960, 2270, 1745, 1455, 1445, 1385, 1305, 1230, 1110 cm$^{-1}$.

An anhydrous toluene solution (30 ml.) of iodopropargyl alcohol (6.60 g., 36.27 mmole) was added to an anhydrous solution (40 ml.) of 2-isocyanatopropionic acid methyl ester (4.64 g., 35.94 mmole) and the reaction mixture was stirred at room temperature for 2.5 hours, then at 70° C. for 17 hours. When cool, the reaction mixture was diluted with toluene and washed with water, 10% aqueous potassium hydrogen sulfate, water, saturated aqueous sodium chloride, dried over magnesium sulfate, filtered and concentrated under reduced pressure to form a yellow crystalline solid (9.55 g., 85.4% crude yield). The crude material was recrystallized from ethyl acetate/hexane to afford N-iodopropargyloxycarbonyl alanine methyl ester (compound 6, 5.85 g.) as a white crystalline solid. m.p. 100°-102° C. 1H-NMR (200 MHz, CDCl$_3$) $\delta_{ppm}$=1.43, d, J=8 Hz., 3H(—CH$_3$), 3.77, s, 3H (—OCH$_3$), 4.38, m, 1H (—CH—CH$_3$), 4.85, d, J=2.7 Hz., 2$\overline{H}$ (—C—CH$_2$—O), 5.39, m, 1$\overline{H}$ (—NH—). IR (CHCl3) 3450, 2970, 2210, 1735, 1515, 1469, 1350, 1080 cm$^{-1}$.

EXAMPLE 6

Preparation of N-Iodopropargyloxycarbonyl Alanine

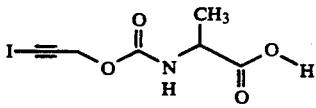

N-iodopropargyloxycarbonyl alanine methyl ester (compound 6, 4.00 g., 12.86 mmole) was dissolved in a tetrahydofuran/water mixture (3:1, 100 ml.) and cooled to 0° C. with an ice bath. Lithium hydroxide (0.35 g., 14.61 mmole) was added and the reaction mixture was stirred for 2 hours. The reaction mixture was filtered, concentrated under reduced pressure, redissolved in water and acidified with 10% aqueous potassium hydrogen sulfate. The aqueous mixture was extracted with methylene chloride several times. The combined methylene chloride layers were washed with water, dried over magnesium sulfate, filtered and concentrated under reduced pressure to afford N-iodopropargyloxycarbonyl alanine (compound 5, 2.72 g., 71.2% yield) as a white crystalline solid. m.p. 95°-99° C.; $^1$H-NMR (200 MHz, DMSOd$_6$) $\delta_{ppm}$=1.28, d, J=8 Hz., 3H (—CH—CH$_3$), 4.00, m, 1H (—CH—CH$_3$), 4.75, s, 2H (—CH$_2$—O), 7.7, d, J=8 Hz., 1H (—NH—), 12.57, s, 1H (—COOH). IR (KBr) 3500-2000, 2200, 1670-1715, 1530, 1450, 1335, 1250, 1075, 1050 cm$^{-1}$.

EXAMPLE 7

Preparation of N-Iodopropargyloxycarbonyl Alanine

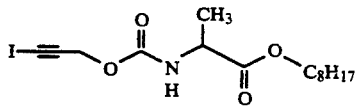

N-iodopropargyloxycarbonyl alanine (compound 5, 0.95 g., 3.20 mmole) was dissolved in anhydrous N,N-dimethylformamide (15 ml.) and treated with the following: n-octanol (0.60 ml., 3.81 mmole), N-(dimethylaminopropyl)-N'-ethylcarbodiimide hydrochloride (0.68 g., 4.07 mmole) and 4-dimethylaminopyridine (0.041 g., 0.336 mmole). The reaction mixture was stirred at room temperature for 10 minutes, then held at 4° C. for 17 hours. The reaction mixture was diluted with ethyl acetate and washed with water, 10% aqueous potassium hydrogen sulfate, water, saturated aqueous sodium carbonate, water, saturated aqueous sodium chloride, dried over magnesium sulfate, filtered and concentrated under reduced pressure to afford an oil. The oil was chromatographed on silica gel (50 g.) and eluted with hexanes/ethyl acetate (9:1) to afford N-iodopropargyloxycarbonyl alanine n-octyl ester (compound 7, 0.97 g., 74% yield) as a clear colorless oil. $^1$H-NMR (200 MHz., CDCl$_3$) $\delta_{ppm}$=0.93, m, 3H (—CH$_2$—CH$_3$), 1.34, m, 10H (—(CH$_2$)$_5$—CH$_3$), 1.47, d, J=8 HZ., 3H (—CH—CH$_3$), 1.7, m, 2H (—CH$_2$—), 4.18, t, J=8 Hz., 2H (—O—CH$_2$—CH$_2$—), 4.4, m, 1H (—CH—CH$_3$), 4.87, s, 2H (—C—CH$_2$—O), 5.42, m, 1H (—NH—). IR (CHCl$_3$) 3440, 2940, 2870, 2210, 1745, 1505, 1455, 1340, 1070 cm$^{-1}$. IR (neat) 3350, 2930, 2860, 2200, 1740, 1515, 1445, 1070 cm$^{-1}$.

EXAMPLE 8

Preparation of N-Iodopropargyloxycarbonyl Phenylalanine Methyl Ester

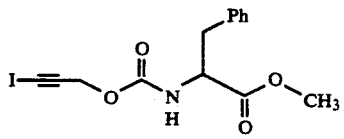

L-Phenylalanine methyl ester hydrochloride (6.00 g., 27.82 mmole) was slurried in anhydrous 1,4-dioxane (125 ml.), treated with trichloromethylchloroformate (5.05 ml., 41.86 mmole) and heated at 55° C. for 17.5 hours. The excess trichloromethylchloroformate and 1,4-dioxane were removed from the reaction mixture by distillation under slightly reduced pressure. The resultant residue was subjected to high vacuum distillation to afford the desired intermediate 2-isocyanato-3-phenylpropionic acid methyl ester (4.78 g., 84% yield). B.P. 83°-85° C. (100 μm Hg.) as a clear colorless liquid. $^1$H-NMR (200 MHz, CDCl$_3$) $\delta_{ppm}$=3.12, dd, J=8.5 Hz., 2H (—CH$_2$—Ph), 3.83, s, 3H (—COOCH$_3$), 4.28, m, 1H (—CH—CH$_2$—), 7.15-7.4, m, 5H (Ar—H).

An anhydrous toluene solution (50 ml.) of iodopropargyl alcohol (4.66 g., 25.61 mmole) was added to an anhydrous toluene solution (50 ml.) of 2-isocyanato-3-phenylpropionic acid methyl ester (4.78 g., 23.29 mmol) containing 5 drops of di-n-butyl tin dilaurate and the reaction mixture was stirred at room temperature for 17 hours. When cool, the reaction mixture was diluted with toluene and washed with water, 10% aqueous potassium hydrogen sulfate, water, saturated aqueous sodium chloride, dried over magnesium sulfate, filtered and concentrated under reduced pressure to form N-iodopropargyloxycarbonyl phenylalanine methyl ester (compound 9) as a white crystalline solid (8.87 g., 98.3% yield). m.p. 100°-103° C.; $^1$H-NMR (200 MHz, CDCL$_3$) $\delta_{ppm}$=3.13, m, 2H (—CH$_2$—Ph), 3.75, s, 3H (COOCH$_3$), 4.65, m, 1H (—CH—), 4.83, s, 2H (C—CH$_2$—O), 5.25, m, 1H (—NH—), 7.05-7.4, m, 5H (Ar—H).

EXAMPLE 9

Preparation of N-Iodopropargyloxycarbonyl Phenylalanine

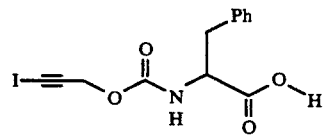

N-iodopropargyloxycarbonyl phenylalanine methyl ester (compound 9, 7.05 g., 18.21 mmole) was dissolved in a tetrahydofuran/water mixture (3:1, 100 ml.) and cooled to 0° C. with an ice bath. Lithium hydroxide (0.483 g., 20.17 mmole) was added and the reaction mixture was stirred for 1.5 hours. An additional amount of lithium hydroxide (45 mg.) was added to the reaction mixture and stirring was continued for 0.5 hr. The reaction mixture was concentrated under reduced pressure to remove the tetrahydrofuran, redissolved in water and acidified with 10% aqueous potassium hydrogen sulfate. The resultant white precipitate was isolated by filtration. The solid waS dissolved in diethyl ether and washed with water, saturated aqueous sodium chloride, dried over magnesium sulfate, filtered and concentrated under reduced pressure to afford N-iodopropargyloxycarbonyl phenylalanine (compound 8, 5.97 g., 87.8% yield) as a white crystalline solid. $^1$H-NMR (200 MHz., DMSOd$_6$) $\delta_{ppm}$=2.95, dd, J=4, 16 Hz., 2H (—CH$_2$—Ph), 4.15, m, 1H (—CH—CH$_2$—), 4.7; s, 2H (—C—CH$_2$—O), 7.3, m, 5H (Ar—H), 7.75,d, J=8 Hz., 1H (—NH—), 12.8, m, 1H (COOH). IR (CHCl$_3$) 3600-2400, 3420, 2200, 1730, 1500, 1065 cm$^{-1}$.

EXAMPLE 10

Preparation of N-Iodopropargyloxycarbonyl Phenylalanine

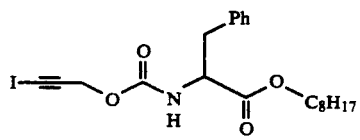

N-iodopropargyloxycarbonyl phenylalanine (compound 8, 2.00 g., 5.36 mmole) was dissolved in anhydrous 1,4-dioxane (20 ml.) and treated with the following: n-octanol (0.95 ml., 6.03 mmole), N-(dimethylaminopropyl)-N'-ethylcarbodiimide hydrochloride (1.08 g., 6.47 mmole) and 4-dimethylaminopyridine (0.073 g., 0.598 mmole). N,N-Dimethylformamide (5.00 ml.) was added to the heterogeneous reaction mixture to effect a homogeneous solution. The reaction mixture was stirred at room temperature for 10 minutes, then held at 4° C. for 17 hours. The reaction mixture was concentrated under reduced pressure to remove the 1,4-dioxane, diluted with methylene chloride and washed with water, 10% aqueous potassium hydrogen sulfate, water, saturated aqueous sodium carbonate, water, saturated aqueous sodium chloride, dried over magnesium sulfate, filtered and concentrated under reduced pressure to afford a viscous pale yellow oil which solidified on standing. The oil was chromatographed on silica gel (70 g.) and eluted with hexanes-/ethyl acetate (9:1) to afford N-iodopropargyloxycarbonyl phenylalanine n-octyl ester (compound 10, 1.98 g., 76.2% yield) as a white crystalline solid. $^1$H-NMR (200 MHz., CDCl$_3$) $\delta_{ppm}$=0.9, m, 3H (—CH$_3$), 1.3, m, 10H (—(CH$_2$)$_5$—CH$_3$), 1.58, m, 2H (—CH$_2$—), 3.13,d, J=5 Hz., 2H (—CH$_2$—Ph), 4.1, t, J=5 Hz., 2H (—O—CH$_2$—CH$_2$—), 4.63, m, 1H (—CH—CH$_2$—), 4.72, s, 2H (C—CH$_2$—O), 5.27, d, J=8 Hz., 1H (—NH—), 7.1-7.35, m, 5H (Ar—H). IR (CHCl3) 3440, 2940, 2870, 1730, 1505, 1355, 1120 cm$^{-1}$.

EXAMPLE 11—BIOLOGICAL ACTIVITY

A. Biocidal Activity:

Biocidal evaluations (bactericidal, algicidal, and fungicidal) were carried out.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm (or 100, 50, 25, 12.5, 6.2, 3.1, 1.6, and 0.8), respectively.

Each vessel is then inoculated with a cell suspension of the appropriate test organism. Bacteria are grown in broth, fungi on agar slants for a time and at a temperature appropriate to the species being tested, and algae are a mixture of green algae and blue-green bacteria grown in a nutrient media. At the end of the growth period, in the case of bacteria, the broth is vortexed to disperse the cells.

In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound.

The algae culture contains green algae and blue-green bacteria, and is obtained from a cooling tower in Spring House, Penn. The algae culture is grown in Allen's medium on a rotary shaker under flourescent room lighting. This culture is further diluted with Allen's medium and then added to the test vessel.

The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity include:

BACTERIA:
*Pseudomonas fluorescens* (PSFL), gram negative
*Pseudomonas aerugenosa* (PSAE), gram negative
*Escherichia coli* (ECOL), gram negative
*Staphylococcus aureus* (SAUR), gram positive
FUNGI:
*Aspergillus niger* (ANIG)
*Aureobasidium pullulans* (APUL)

The results of the minimum inhibitory concentration (MIC) tests of compounds of this invention are shown in Table I against the microorganisms shown in Table II.

TABLE 1

BIOCIDES SECONDARY MIC TEST DATA IN PPM
These compounds were tested in M9G
(minimal salts media with glucose)

| Compound # | (G−) PSFL | (G−) PSAE | (G−) ECOL | (G+) SAUR | (F) ANIG | (F) APUL | ALGAE |
|---|---|---|---|---|---|---|---|
| 1 | 250 | >500 | 250 | 250 | >500 | >500 | |
| 2 | 16 | 32 | 32 | 16 | <4 | <4 | |
| 3 | 8 | >500 | >500 | 8 | <4 | <4 | |
| 4 | 32 | 125 | 125 | 32 | <0.12 | <0.12 | 12.5 |
| 5 | 125 | >500 | 125 | 250 | 125 | 32 | |
| 6 | <4 | 32 | <4 | 16 | <4 | <4 | |
| 7 | 8 | 125 | <4 | 63 | <4 | <63 | |
| 8 | 63 | 250 | <4 | 125 | 250 | 250 | |
| 9 | 125 | >500 | >500 | 125 | <4 | <4 | |
| 10 | 32 | 63 | <4 | 32 | 125 | 125 | |

TABLE II

| MICROORGANISMS USED IN THE BIOCIDES TESTS | | |
|---|---|---|
| NAME | GRAM ATCC No. | Abbreviation used |
| BACTERIA | | |
| 1. *Pseudomonas aeruginosa* (−) | 15442 | PSAE |
| 2. *Staphylococcus aureus* (+) | 6538 | SAUR |
| 3. *Escherichia coli* (−) | 11229 | ECOL |

TABLE II-continued

| MICROORGANISMS USED IN THE BIOCIDES TESTS | | |
|---|---|---|
| NAME | GRAM ATCC No. | Abbreviation used |
| 4. *Pseudomonas fluorescens* (−) | 948 | PSFL |
| FUNGI | | |
| 5. *Aspergillus niger* | 6275 | ANIG |
| 6. *Aureobasidium pullulans* | 9348 | APUL |

We claim:

1. Compounds of the formula

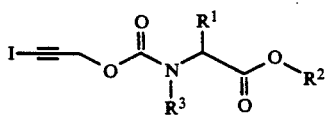

wherein $R^1$ is selected from the group consisting of H, lower $(C_1-C_4)$alkyl, alkyl aryl, $CH_2OR$, $CH_2SR$, and $CH(CH_3)OR$; and R, $R^2$, and $R^3$ are independently selected from H, $(C_1-C_4)$alkyl, aryl, arylalkyl, alkaryl, and halopropargyl.

2. Compound according to claim 1 wherein said compound is selected from the group consisting of N-iodopropargyloxycarbonyl glycine methyl ester; N-iodopropargyloxycarbonyl glycine; N-iodopropargyloxycarbonyl glycine n-octyl ester; N-iodopropargyloxycarbonyl glycine iodopropargyl ester; N-iodopropargyloxycarbonyl alanine methyl ester; N-iodopropargyloxycarbonyl alanine; N-iodopropargyloxycarbonyl alanine n-octyl ester; N-iodopropargyloxycarbonyl phenylalanine methyl ester; N-iodopropargyloxycarbonyl pheylalanine; N-iodopropargyloxycarbonyl phenylalanine; and n-octyl ester.

3. Process for preventing or controlling the growth of microorganisms in a locus comprising introducing or applying a microbicidally effective amount of a compound according to claim 1 as an antimicrobial agent at, into, or onto said locus.

4. Process according to claim 1 wherein said microorganism is bacteria, fungi, and/or algae.

5. Process comprising using a compound according to claim 1 to control industrial fungi.

6. Process comprising using a compound according to claim 1 to control bacteria.

7. Process according to claim 1 wherein said microorganism is algae, viruses or yeasts.

8. Process according to claim 1 wherein said locus is a material selected from the group consisting of wood, paint, adhesive, glue, paper, textile, leather, plastics, cardboard, lubricants, cosmetics, food, caulking, feed and industrial cooling water.

9. Process according to claim 1 wherein said compound is used as a topical antifungal and/or antibacterial agent on human skin.

* * * * *